(12) United States Patent
Day

(10) Patent No.: US 9,872,854 B2
(45) Date of Patent: Jan. 23, 2018

(54) METHODS FOR THE TREATMENT OF PSORIATIC ARTHRITIS USING APREMILAST

(71) Applicant: CELGENE CORPORATION, Summit, NJ (US)

(72) Inventor: Robert Day, Newtown, PA (US)

(73) Assignee: Celgene Corporation, Summit, NJ (US)

( * ) Notice: Subject to any disclaimer, the term of this patent is extended or adjusted under 35 U.S.C. 154(b) by 77 days.

(21) Appl. No.: 14/209,874

(22) Filed: Mar. 13, 2014

(65) Prior Publication Data

US 2014/0301980 A1 Oct. 9, 2014
US 2015/0174100 A2 Jun. 25, 2015

Related U.S. Application Data

(60) Provisional application No. 61/782,880, filed on Mar. 14, 2013.

(51) Int. Cl.
*A61K 31/4035* (2006.01)
*A61K 45/06* (2006.01)

(52) U.S. Cl.
CPC .......... *A61K 31/4035* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 5,059,595 A | 10/1991 | Le Grazie | |
| 5,073,543 A | 12/1991 | Marshall et al. | |
| 5,120,548 A | 6/1992 | McClelland et al. | |
| 5,354,556 A | 10/1994 | Sparks et al. | |
| 5,591,767 A | 1/1997 | Mohr et al. | |
| 5,639,476 A | 6/1997 | Oshlack et al. | |
| 5,674,533 A | 10/1997 | Santus et al. | |
| 5,733,566 A | 3/1998 | Lewis | |
| 6,020,358 A | 2/2000 | Muller et al. | |
| 6,962,940 B2 | 11/2005 | Muller et al. | |
| 7,208,516 B2 | 4/2007 | Muller et al. | |
| 7,276,529 B2 | 10/2007 | Muller et al. | |
| 7,358,272 B2 | 4/2008 | Muller et al. | |
| 7,427,638 B2 | 9/2008 | Muller et al. | |
| 7,507,759 B2 | 3/2009 | Muller et al. | |
| 7,659,302 B2 | 2/2010 | Muller et al. | |
| 7,659,303 B2 | 2/2010 | Muller et al. | |
| 7,893,101 B2 | 2/2011 | Muller et al. | |
| 8,093,283 B2 | 1/2012 | Muller et al. | |
| 8,455,536 B2 | 6/2013 | Muller et al. | |
| 8,629,173 B2 | 1/2014 | Muller et al. | |
| 2006/0148882 A1 | 7/2006 | Zeldis et al. | |
| 2006/0183787 A1 | 8/2006 | Muller et al. | |
| 2008/0234359 A1 | 9/2008 | Muller et al. | |
| 2009/0186923 A1* | 7/2009 | Armer | C07D 401/06 514/339 |
| 2009/0239926 A1 | 11/2009 | Schafer et al. | |
| 2010/0168475 A1 | 7/2010 | Saindane et al. | |
| 2014/0024695 A1 | 1/2014 | Muller et al. | |
| 2014/0100259 A1 | 4/2014 | Muller et al. | |

FOREIGN PATENT DOCUMENTS

| | | |
|---|---|---|
| WO | 03/080049 A1 | 10/2003 |
| WO | 2006/065814 A1 | 6/2006 |

OTHER PUBLICATIONS

Papp et al. (The Lancet, 380(9843), 738-746, 2012).*
International Search Report issued in PCT Application No. PCT/US2014/025171 dated Jun. 12, 2014.
Anonymous, "A Phase 3, Multicenter, Randomized, Double-Blind, Placebo-Controlled, Parallel-Group, Efficacy and Safety Study of Two Doses of Apremilast (CC-10004) in Subjects With Active Psoriatic Arthritis Who Have Not Been Previously Treated With Disease Modifying Anti-rheumatic Drugs," retrieved from http://clinicaltrials.gov/archive/NCT01307423/2012_09_06 on May 22, 2014.
Schett et al., "Oral Apremilast in the Treatment of Active Psoriatic Arthritis," *Arthritis & Rheumatism*, 64(10):3156-3167 (2012).
Registry, Oct. 23, 2003, XP002526542, whole document.
U.S. Appl. No. 60/366,515, filed Mar. 20, 2002, Schafer et al.
U.S. Appl. No. 60/438,450, filed Jan. 7, 2003, Schafer et al.
U.S. Appl. No. 60/634,982, filed Dec. 13, 2004, Zeldis et al.
Beavo and Reitsnyder, "Primary sequence of cyclic nucleotide phosphodiesterase isozymes and the design of selective inhibitors," Trends Pharmcol. Sci., 11(4):150-155 (1990).
Carstensen, Drug Stability: Principles & Practices, Second Edition, Marcel Dekker, New York, NY, pp. 379-380 (1995).
Dong et al., "Inhibition of PDE3, PDE4 and PDE7 potentiates glucocorticoid-induced apoptosis and overcomes glucocorticoid resistance in CEM T leukemic cells," Biochem. Pharmacol., 79(3):321-329 (2010).

(Continued)

*Primary Examiner* — Bong-Sook Baek
(74) *Attorney, Agent, or Firm* — Jones Day

(57) ABSTRACT

Methods of treating, managing or preventing psoriatic arthritis are disclosed. Specific methods encompass the administration of apremilast, alone or in combination with a second active agent.

30 Claims, No Drawings

(56) References Cited

OTHER PUBLICATIONS

Fox et al., "Combined oral cyclosporin and methotrexate therapy in patients with rheumatoid arthritis elevates methotrexate levels and reduces 7-hydroxymethotrexate levels when compared with methotrexate alone," Rheumatology (Oxford), 42(8):989-994 (2003).
Gladman et al., Kelley's Textbook of Rheumatology, 2 Vols. 6th Edition, W. B. Saunders Company, Chapter 71, pp. 1071-1077 (2001).
Gladman, "Current concepts in psoriatic arthritis," Curr. Opin. Rheumatol., 14(4):361-366 (2002).
Kowalczyk et al., "Effect of phosphodiesterase antagonists on glucocorticoid mediated growth inhibition in murine skin cell lines," Eur. J. Pharmacol., 610(1-3):29-36 (2009).
Long et al., "Human articular chondrocytes produce IL-7 and respond to IL-7 with increased production of matrix metalloproteinase-13," Arthritis Res. Ther., 10(1):R23 (2008).
Lowe et al., "Patent evaluation: novel dioxolanes as cholesterol lowering agents," Exp. Opin. Ther. Patents, 2 (8):1309-1310 (1992).
Lowe et al., Drugs of the Future, 17(9):799-807 (1992).
McCann et al., "Apremilast, a novel PDE4 inhibitor, inhibits spontaneous production of tumour necrosis factor-alpha from human rheumatoid synovial cells and ameliorates experimental arthritis," Arthritis Res. Ther., 12(3):R107 (2010).
Meyers et al., "Phosphodiesterase 4 inhibitors augment levels of glucocorticoid receptor in B cell chronic lymphocytic leukemia but not in normal circulating hematopoietic cells," Clin. Cancer Res., 13(16):4920-4927 (2007).
Patel et al., "Psoriatic arthritis—emerging concepts," Rheumatology (Oxford), 40(3):243-246 (2001).
Rihl et al., "Identification of interleukin-7 as a candidate disease mediator in spondylarthritis," Arthritis Rheum., 58 (11):3430-3435 (2008).
The Merck Manual, 17th Edition, Merck & Company, West Point, PA, pp. 448, 944-952 (1999).
Tierney et al. (eds), Current Medical Diagnosis & Treatment 1998, 37th Edition, Appleton & Lange, Stamford, CT, p. 793 (1998).
Verghese et al., "Differential regulation of human monocyte-derived TNF alpha and IL-1 beta by type IV cAMP-phosphodiesterase (cAMP-PDE) inhibitors," J. Pharmacol. Exp. Ther., 272(3), 1313-1320 (1995).
Wilen et al., "Strategies in optical resolutions," Tetrahedron, 33:2725-2736 (1977).
Wilen, Tables of Resolving Agents and Optical Resolutions, (E.L. Eliel, Ed.), University of Notre Dame Press, Notre Dame, IN, p. 268 (1972).
Wolff ed., Burger's Medicinal Chemistry and Drug Discovery, 5th Edition, John Wiley & Sons, Inc., pp. 172-178, 949-982 (1995).

* cited by examiner

METHODS FOR THE TREATMENT OF PSORIATIC ARTHRITIS USING APREMILAST

This application claims the benefit of U.S. Provisional Patent Application No. 61/782,880, filed on Mar. 14, 2013, the entirety of which is hereby incorporated by reference.

1. FIELD

Provided herein are methods for treating, preventing and/or managing psoriatic arthritis by the administration of apremilast, alone or in combination with other therapeutics. Also provided herein are pharmaceutical compositions and dosage forms comprising specific amounts of apremilast suitable for use in methods of treating, preventing and/or managing psoriatic arthritis.

2. BACKGROUND

Psoriatic arthritis is a chronic inflammatory arthritic condition affecting the skin, the joints, the insertion sites of tendons, ligaments, and fascia. Gladman, *Current Opinion in Rheumatology*, "Current concepts in psoriatic arthritis," 2002, 14:361-366, and Ruddy et al., *Rheumatology*, vol. 2., chapter 71, page 1071, 6$^{th}$ ed., 2001. Psoriatic arthritis is commonly associated with psoriasis. Id. Approximately 7% of patients with psoriasis develop psoriatic arthritis. *The Merck Manual*, 448 (17$^{th}$ ed., 1999).

Psoriatic arthritis may appear in a variety of clinical patterns. There are five general patterns of psoriatic arthritis: arthritis of the distal interphalangeal joints, destructive arthritis, symmetric polyarthritis indistinguishable from rheumatoid arthritis, asymmetric oligoarthritis, and spondyloarthropathy. Ruddy et al., page 1073. Psoriasis appears to precede the onset of psoriatic arthritis in 60-80% of patients. Occasionally, arthritis and psoriasis appear simultaneously. Cutaneous eruptions may be preceded by the arthropathy.

Symptoms of psoriatic arthritis include extra bone formation, joint stiffness, dactylitis, enthesopathy, tendonitis, and spondylitis. Gladman, page 362. Most patients have the classic psoriasis pattern of skin lesions. Ruddy et al., page 1075. Scaly, erythematous plaques; guttate lesions, lakes of pus, and erythroderma are psoriatic skin lesions that may be seen in patients with psoriatic arthritis. Nail lesions, including pitting, Beau lines, leukonychia, onycholysis, oil spots, subungual hyperkeratosis, splinter hemorrhages, spotted lunulae, and cracking, are clinical features significantly associated with the development of psoriatic arthritis. Ruddy et al., page 1076. Ocular symptoms in psoriatic arthritis include conjunctivitis, iritis, episcleritis, keratoconjunctivitis sicca and aortic insufficiency.

Although the exact cause of psoriatic arthritis is unknown, genetic, environmental, immunologic, and vascular factors contribute to one's predisposition. Ruddy et al., pages 1071-72, and Gladman, page 363. The disease is more likely to occur in first-degree relatives who are affected than in the general population. Ruddy et al., page 1071. Population studies have shown that multiple human leukocyte antigens (HLA) are associated. British Society for Rheumatology, *Rheumatology*, 2001; 40:243, and Gladman, page 362. Much evidence suggests that a T-cell—mediated process drives the pathophysiology of psoriatic arthritis. Ruddy et al., pages 1071 and 1077, and Gladman, page 363. Activated T cells may contribute to the enhanced production of cytokines found in synovial fluid. Th1 cytokines (e.g., tumor necrosis factor-alpha (TNF-alpha), interleukin (IL)-1-beta and IL-10) are more prevalent in psoriatic arthritis than in rheumatoid arthritis, suggesting that the two diseases may result from a different mechanism. Ruddy et al., page 1071. Monocytes also play a role in psoriatic arthritis and are responsible for the production of matrix metalloproteinases, which may mediate the destructive changes in the joints of patients with psoriatic arthritis. Gladman, page 364.

Internationally, the incidence of psoriatic arthritis is 1-40%. Psoriatic arthritis usually develops in the fourth to sixth decades of life, but it can occur at almost any age. Men and women are affected equally, but a male predominance occurs in the spondylitic form, while a female predominance occurs in the rheumatoid form. Ruddy et al., page 1077.

There is a significant need for safe and effective methods of treating, preventing and managing psoriatic arthritis, particularly for patients that are refractory to conventional treatments. In addition, there is a need to treat such disease while reducing or avoiding the toxicity and/or side effects associated with conventional therapies.

3. SUMMARY

Provided herein are methods for treating methods of treating, preventing and/or managing psoriatic arthritis in humans in need thereof. The methods comprise administering to a patient in need of such treatment, prevention or management a therapeutically or prophylactically effective amount of apremilast, or a pharmaceutically acceptable prodrug, metabolite, polymorph, salt, solvate (e.g., hydrate) or clathrate thereof.

In some embodiments, provided herein is a method of treating psoriatic arthritis, which comprises orally administering to a patient having psoriatic arthritis escalating doses of stereomerically pure (+)-2-[1-(3-ethoxy-4-methoxyphenyl)-2-methylsulfonylethyl]-4-acetylaminoisoindoline-1,3-dione, or a pharmaceutically acceptable prodrug, polymorph, salt, or solvate thereof, wherein a starting dose is between about 10 mg/day and about 20 mg/day, and a maximum dose is between about 40 mg/day and about 100 mg/day.

In some embodiments, the method comprises the following initial titration schedule:
(i) 10 mg in the morning on the first day of administration;
(ii) 10 mg in the morning and 10 mg after noon on the second day of administration;
(iii) 10 mg in the morning and 20 mg after noon on the third day of administration;
(iv) 20 mg in the morning and 20 mg after noon on the fourth day of administration;
(v) 20 mg in the morning and 30 mg after noon on the fifth day of administration; and
(vi) 30 mg in the morning and 30 mg after noon on the sixth and every subsequent day of administration.

In some embodiments, the methods further comprise the administration of a therapeutically or prophylactically effective amount of at least a second active agent, including but not limited to, an anti-inflammatory agent, an immnunosuppressant, mycophenolate mofetil, a biologic agent, or a Cox-2 inhibitor.

In another embodiment, apremilast, or a pharmaceutically acceptable prodrug, metabolite, polymorph, salt, solvate (e.g., hydrate) or clathrate thereof is administered orally in a dosage form such as a tablet and a capsule.

4. DETAILED DESCRIPTION

4.1 Definitions

As used herein, the term "apremilast" refers to (+)-2-[1-(3-ethoxy-4-methoxyphenyl)-2-methylsulfonylethyl]-4- acetylaminoisoindoline-1,3-dione, also known as N-[2-[(1S)-1-(3-ethoxy-4-methoxyphenyl)-2-(methylsulfonyl) ethyl]-2,3-dihydro-1,3-dioxo-1H-isoindol-4-yl]acetamide. Apremilast has the following structure:

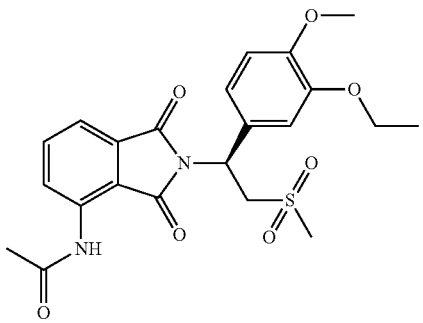 [SMILES: CCOc1cc([C@@H](CS(C)(=O)=O)N2C(=O)c3cccc(NC(C)=O)c3C2=O)ccc1OC]

As used herein and unless otherwise indicated, the term "pharmaceutically acceptable salt" includes, but is not limited to, salts prepared from pharmaceutically acceptable non-toxic acids or bases including inorganic acids and bases and organic acids and bases. Suitable pharmaceutically acceptable base addition salts provided herein include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts.

As used herein and unless otherwise indicated, the term "hydrate" means a compound provided herein or a salt thereof, that further includes a stoichiometric or non-stoichiometric amount of water bound by non-covalent intermolecular forces.

As used herein and unless otherwise indicated, the term "solvate" means a solvate formed from the association of one or more solvent molecules to a compound provided herein. The term "solvate" includes hydrates (e.g., monohydrate, dihydrate, trihydrate, tetrahydrate and the like).

As used herein and unless otherwise indicated, the term "polymorph" means solid crystalline forms of a compound provided herein or complex thereof. Different polymorphs of the same compound can exhibit different physical, chemical and/or spectroscopic properties.

As used herein and unless otherwise specified, the term "prodrug" means a derivative of a compound that can hydrolyze, oxidize, or otherwise react under biological conditions (in vitro or in vivo) to provide the compound. Examples of prodrugs include, but are not limited to, derivatives and metabolites of apremilast that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Prodrugs can typically be prepared using well-known methods, such as those described by 1 *Burger's Medicinal Chemistry and Drug Discovery*, 172-178, 949-982 (Manfred E. Wolff ed., 5th ed. 1995).

As used herein, and unless otherwise specified, the term "enantiomer," "isomer" or "stereoisomer" encompasses all enantiomerically/stereomerically pure and enantiomerically/stereomerically enriched compounds provided herein.

As used herein, and unless otherwise indicated, the term "stereomerically pure" or "enantiomerically pure" means that a compound comprises one stereoisomer and is substantially free of its counter stereoisomer or enantiomer. For example, a compound is stereomerically or enantiomerically pure, when the compound contains greater than or equal to 80%, 90%, 95%, 96%, 97%, 98% or 99% of one stereoisomer, and 20%, 10%, 5%, 4%, 3%, 2%, 1% or less of the counter stereoisomer. "Substantially free of its (R) enantiomer" is encompassed by the term stereomerically pure or enantiomerically pure.

As used herein, term "adverse effect" includes, but is not limited to gastrointestinal, renal and hepatic toxicities, leukopenia, increases in bleeding times due to, e.g., thrombocytopenia, and prolongation of gestation, nausea, vomiting, somnolence, asthenia, dizziness, teratogenicity, extra-pyramidal symptoms, akathisia, cardiotoxicity including cardiovascular disturbances, inflammation, male sexual dysfunction, and elevated serum liver enzyme levels. The term "gastrointestinal toxicities" includes but is not limited to gastric and intestinal ulcerations and erosions. The term "renal toxicities" includes but is not limited to such conditions as papillary necrosis and chronic interstitial nephritis.

As used herein, the term "patient" refers to a mammal, particularly a human. In some embodiments, the patient is a female. In further embodiments, the patient is a male. In further embodiments, the patient is a child.

As used herein, and unless otherwise specified, the terms "treat," "treating" and "treatment" contemplate an action that occurs while a patient is suffering from the specified disease or disorder, which reduces the severity or symptoms of the disease or disorder, or retards or slows the progression or symptoms of the disease or disorder.

As used herein, unless otherwise specified, the terms "prevent," "preventing" and "prevention" contemplate an action that occurs before a patient begins to suffer from the specified disease or disorder, which inhibits or reduces the severity or symptoms of the disease or disorder.

As used herein, and unless otherwise indicated, the terms "manage," "managing," and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

4.2 Methods of Treatment and Prevention

Provided herein are methods of treating, managing and/or preventing psoriatic arthritis, which comprise administering to a patient in need of such treatment, management or prevention a therapeutically or prophylactically effective amount of apremilast, or a pharmaceutically acceptable prodrug, metabolite, polymorph, salt, solvate or clathrate thereof.

In some embodiments, the methods also encompass inhibiting or averting symptoms of psoriatic arthritis as well as addressing the disease itself, prior to the onset of symptoms by administering apremilast, or a pharmaceutically acceptable prodrug, metabolite, polymorph, salt, solvate or clathrate thereof. Patients having history of psoriasis or psoriatic arthritis are preferred candidates for preventive regimens.

In certain embodiments, apremilast is orally administered to a patient having psoriatic arthritis in a twice daily dose of 30 mg per day.

In some embodiments, provided herein is a method of treating psoriatic arthritis, which comprises orally administering to a patient having psoriatic arthritis escalating doses of stereomerically pure (+)-2-[1-(3-ethoxy-4-methoxyphenyl)-2-methylsulfonylethyl]-4-acetylaminoisoindoline-1,3-dione, or a pharmaceutically acceptable prodrug, polymorph, salt, or solvate thereof, wherein a starting dose is between about 10 mg/day and about 20 mg/day, and a maximum dose is between about 40 mg/day and about 100 mg/day.

In some embodiments, the method comprises the following initial titration schedule:

(i) 10 mg in the morning on the first day of administration;

(ii) 10 mg in the morning and 10 mg after noon on the second day of administration;

(iii) 10 mg in the morning and 20 mg after noon on the third day of administration;

(iv) 20 mg in the morning and 20 mg after noon on the fourth day of administration;

(v) 20 mg in the morning and 30 mg after noon on the fifth day of administration; and (vi) 30 mg in the morning and 30 mg after noon on the sixth and every subsequent day of administration.

In some embodiments, the dosing schedule may be represented as follows:

| Day 1 | Day 2 | | Day 3 | | Day 4 | | Day 5 | | Day 6 & thereafter | |
|---|---|---|---|---|---|---|---|---|---|---|
| AM | AM | PM | AM | PM | AM | PM | AM | PM | AM | PM |
| 10 mg | 10 mg | 10 mg | 10 mg | 20 mg | 20 mg | 20 mg | 20 mg | 30 mg | 30 mg | 30 mg |

In one embodiment, stereomerically pure apremilast, (+)-2-[1-(3-ethoxy-4-methoxyphenyl)-2-methylsulfonylethyl]-4-acetylaminoisoindoline-1,3-dione, is administered according the above schedule.

In some embodiments, the stereomerically pure (+)-2-[1-(3-ethoxy-4-methoxyphenyl)-2-methylsulfonylethyl]-4-acetylaminoisoindoline-1,3-dione comprises greater than about 90% by weight of (+) isomer based on the total weight percent of the compound.

In some embodiments, the stereomerically pure (+)-2-[1-(3-ethoxy-4-methoxyphenyl)-2-methylsulfonylethyl]-4-acetylaminoisoindoline-1,3-dione comprises greater than about 95% by weight of (+) isomer based on the total weight percent of the compound.

In some embodiments, the stereomerically pure (+)-2-[1-(3-ethoxy-4-methoxyphenyl)-2-methylsulfonylethyl]-4-acetylaminoisoindoline-1,3-dione comprises greater than about 96% by weight of (+) isomer based on the total weight percent of the compound.

In some embodiments, the stereomerically pure (+)-2-[1-(3-ethoxy-4-methoxyphenyl)-2-methylsulfonylethyl]-4-acetylaminoisoindoline-1,3-dione comprises greater than about 97% by weight of (+) isomer based on the total weight percent of the compound.

In some embodiments, the stereomerically pure (+)-2-[1-(3-ethoxy-4-methoxyphenyl)-2-methylsulfonylethyl]-4-acetylaminoisoindoline-1,3-dione comprises greater than about 98% by weight of (+) isomer based on the total weight percent of the compound.

In some embodiments, the stereomerically pure (+)-2-[1-(3-ethoxy-4-methoxyphenyl)-2-methylsulfonylethyl]-4-acetylaminoisoindoline-1,3-dione comprises greater than about 99% by weight of (+) isomer based on the total weight percent of the compound.

In some embodiments, the stereomerically pure (+)-2-[1-(3-ethoxy-4-methoxyphenyl)-2-methylsulfonylethyl]-4-acetylaminoisoindoline-1,3-dione is administered in an amount of about 20 mg twice a day following the initial titration schedule.

In some embodiments, the stereomerically pure (+)-2-[1-(3-ethoxy-4-methoxyphenyl)-2-methylsulfonylethyl]-4-acetylaminoisoindoline-1,3-dione is administered in an amount of about 30 mg twice a day following the initial titration schedule.

In some embodiments, the stereomerically pure (+)-2-[1-(3-ethoxy-4-methoxyphenyl)-2-methylsulfonylethyl]-4-acetylaminoisoindoline-1,3-dione is administered once or twice daily.

In some embodiments, the stereomerically pure (+)-2-[1-(3-ethoxy-4-methoxyphenyl)-2-methylsulfonylethyl]-4-acetylaminoisoindoline-1,3-dione is administered in tablet form. In some embodiments, the tablet comprises a 10 mg, 20 mg or 30 mg dose of stereomerically pure (+)-2-[1-(3-ethoxy-4-methoxyphenyl)-2-methylsulfonylethyl]-4-acetylaminoisoindoline-1,3-dione.

In some embodiments, the methods provided herein, further comprise administering to the patient a therapeutically effective amount of a second active agent. In some embodiments, the second active agent is an anti-inflammatory agent, an immnunosuppressant, mycophenolate mofetil, a biologic agent, or a Cox-2 inhibitor. In some embodiments, the second active agent is a nonsteroidal anti-inflammatory agent. In some embodiments, the second active agent is a disease-modifying anti-rheumatic agent. In some embodiments, the second active agent is methotrexate. In some embodiments, the second active agent is sulfasalazine. In some embodiments, the second active agent is lefunomide. In some embodiments, the second active agent is etanercept. In some embodiments, the second active agent is an oral corticosteroid. In some embodiments, the second active agent is prednisone.

In some embodiments, the patient has received prior treatment for psoriatic arthritis. In some embodiments, the prior treatment is with a disease—modifying antirheumatic drug. In some embodiments, the psoriatic arthritis is refractory to the prior treatment.

In some embodiments, the psoriatic arthritis is symmetric polyarthritis, asymmetric oligoarthritis, distal interphalangeal joint arthritis, arthritis mutilans, or predominant spondylitis.

In some embodiments, the method comprises administering stereomerically pure (+)-2-[1-(3-ethoxy-4-methoxyphenyl)-2-methylsulfonylethyl]-4-acetylaminoisoindoline-1,3-dione, substantially free of any salt, solvate, or prodrug forms of (+)-2-[1-(3-ethoxy-4-methoxyphenyl)-2-methylsulfonylethyl]-4-acetylaminoisoindoline-1,3-dione.

In some embodiments, the method comprises administering a pharmaceutically acceptable salt of stereomerically pure (+)-2-[1-(3-ethoxy-4-methoxyphenyl)-2-methylsulfonylethyl]-4-acetylaminoisoindoline-1,3-dione.

In some embodiments, the method comprises administering a pharmaceutically acceptable solvate of stereomerically pure (+)-2-[1-(3-ethoxy-4-methoxyphenyl)-2-methylsulfonylethyl]-4-acetylaminoisoindoline-1,3-dione.

4.2.1 Combination Therapy

In particular methods encompassed by this embodiment, apremilast is administered in combination with another drug ("second active agent") for treating, managing and/or preventing psoriatic arthritis or psoriasis.

In certain embodiments, the methods encompass synergistic combinations for the treatment, prevention and/or management of psoriasis or psoriatic arthritis. Apremilast may also be used to alleviate adverse effects associated with some second active agents.

One or more second active agents can be used in the methods together with apremilast. Second active agents can be administered before, after or simultaneously with apremilast. In some embodiments, the one or more second active agents are selected from the group consisting of anti-inflammatories such as nonsteroidal anti-inflammatory drugs (NSAIDs), immnunosuppressants, topical steroids, glucocorticoids, calcineurin inhibitors, Cox-2 inhibitors, TNF-alpha inhibitors, antirheumatics, antipsoriatics, interleukin inhibitors, narcotic analgesic combinations, salicylates, glucocorticoids and topical rubefacients.

In one embodiment, the second active agent is selected from the group consisting of an anti-inflammatory agent, an immnunosuppressant, mycophenolate mofetil, a biologic agent, or a Cox-2 inhibitor.

In one embodiment, the second active agent is sulfasalazine.

In one embodiment, the second active agent is lefunomide.

In one embodiment, the second active agent is an oral corticosteroid.

In one embodiment, the second active agent is etanercept.

In some embodiments, the second active agents may include, but are not limited to, anti-inflammatories such as NSAIDs including, but not limited to, diclofenac (e.g., ARTHROTEC®), diflunisal (e.g., DOLOBID®), etodolac (e.g., LODINE®), fenoprofen (e.g., NALFON®), ibuprofen (e.g., ADVIL, CHILDREN'S ADVIL/MOTRIN, MEDIPREN, MOTRIN, NUPRIN or PEDIACARE FEVER®), indomethacin (e.g., ARTHREXIN®), ketoprofen (e.g., ORUVAIL®), ketorolac (e.g., TORADOL®), fosfomycin tromethamine (e.g., MONURAL®), meclofenamate (e.g., Meclomen®), nabumetone (e.g., RELAFEN®), naproxen (e.g., ANAPROX®, ANAPROX® DS, EC-NAPROSYN®, NAPRELAN® or NAPROSYN®), oxaprozin (e.g., DAYPRO®), piroxicam (e.g., FELDENE®), sulindac (e.g., CLINORIL®), and tolmetin (e.g., TOLECTIN® DS or TOLECTIN®).

In other embodiments, the second active agents may include, but are not limited to, disease-modifying antirheumatic drugs (DMARDs) or immnunosuppressants such as, but not limited to, methotrexate (Rheumatrex®), sulfasalazine (Azulfidine®), lefunomide (Arava®), and cyclosporine (Sandimmune® or Neoral®).

In other embodiments, the second active agent is an oral corticosteroid, such as, but not limited to, budesonide (Entocort®), dexamethazone, fludrocortisone (Florinef®, Florinef® acetate), hydrocortisone, methylprednisone, prednisolone, and prednisone.

In other embodiments, the second active agents may include, but are not limited to, mycophenolate mofetil (CellCept®), an immunosuppressive agent widely used in organ transplantation and gaining favor in treating autoimmune and inflammatory skin disorders.

In further embodiments, the second active agents may include, but are not limited to, biologic agents such as etanercept (Enbrel®), infliximab (Remicade®) and adalimumab (Humira®).

In further embodiments, the second active agents may include, but are not limited to, Cox-2 inhibitors such as celecoxib (Celebrex®), valdecoxib (Bextra®) and meloxicam (Mobic®).

In some embodiments, the one or more selective active agents is selected from the group consisting of acitretin, adalimumab, alclometasone, alefacept, aloe vera, amcinonide, ammonium lactate/urea, ammonium lactate/halobetasol, anthralin, benzocaine/pyrilamine/zinc oxide, betamethasone, betamethasone/calcipotriene, calcipotriene, clobetasol, clocortolone, coal tar, coal tar/salicylic acid, corticotropin, cyclosporine, desonide, desoximetasone, diflorasone, fluocinonide, flurandrenolide, halcinonide, halobetasol, hydrocortisone, hydrocortisone/pramoxine, hydroxyurea, infliximab, methotrexate, methoxsalen, mometasone, pramoxine, prednisone, prednisolone, prednicarbate, resorcinol, tazarotene, triamcinolone and ustekinumab.

In some embodiments, the one or more selective active agents is selected from the group consisting of abatacept, acetaminophen, acetaminophen/hydrocodone, acetaminophen/tramadol, adalimumab, alemtuzumab, aluminum hydroxide/aspirin/calcium carbonate/magnesium hydroxide, anakinra, aspirin, auranofin, aurothioglucose, atorvastatin, azathioprine, celecoxib, certolizumab, chondroitin, cortisone, corticotropin, cyclophosphamide, cyclosporine, daclizumab, dexamethazone, diclofenac, diclofenac/misoprostol, diflunisal, doxycycline, esomeprazole, esomeprazole/naproxen, etanercept, etodolac, famotidine, famotidine/ibuprofen, fenoprofen, flurbiprofen, glucosamine, gold sodium thiomalate, golimumab, hydroxychloroquine, ibuprofen, indomethacin, infliximab, interferon, interferon gamma-1b, ketoprofen, lansoprazole, lansoprazole/naproxen, lefunomide, levamisole, meclofenamate, meloxicam, methotrexate, methylprednisone, methylprednisolone, methyl salicylate, minocycline, mycophenolate mofetil, nabumetone, naproxen, oxaprozin, penicillamine, phenytoin, piroxicam, prednisone, primrose oil, rituximab, rofecoxib, salsalate, sulindac, sulfasalazine, tetracycline, tocilizumab, tofacitinib, tolmetin, tramadol, triamcinolone, trolamine salicylate and valdecoxib.

In some embodiments, the one or more selective active agents is selected from the group consisting of abatacept, acetaminophen, acetaminophen/hydrocodone, acetaminophen/tramadol, acitretin, adalimumab, alclometasone, alefacept, alemtuzumab, aloe vera, aluminum hydroxide/aspirin/calcium carbonate/magnesium hydroxide, amcinonide, ammonium lactate/urea, ammonium lactate/halobetasol, anakinra, anthralin, aspirin, auranofin, aurothioglucose, atorvastatin, azathioprine, benzocaine/pyrilamine/zinc oxide, betamethasone, betamethasone/calcipotriene, calcipotriene, celecoxib, certolizumab, chondroitin, clobetasol, clocortolone, coal tar, coal tar/salicylic acid, corticotropin, cortisone, cyclophosphamide, cyclosporine, daclizumab, desonide, desoximetasone, dexamethasone, diclofenac, diclofenac/misoprostol, diflorasone, diflunisal, doxycycline, esomeprazole, esomeprazole/naproxen, etanercept, etodolac, famotidine, famotidine/ibuprofen, fenoprofen, fluocinonide, flurandrenolide, flurbiprofen, fostamatinib, glucosamine, gold sodium thiomalate, golimumab, halcinonide, halobetasol, hydrocortisone, hydrocortisone/pramoxine, hydroxyurea, hydroxychloroquine, ibuprofen, indomethacin, infliximab, interferon, interferon gamma-1b, ibrutinib, ketoprofen, lansoprazole, lansoprazole/naproxen, leflunomide, lenalidomide, levamisole, meclofenamate, meloxicam, methotrexate, methoxsalen, methylprednisone, methylprednisolone, methyl salicylate, minocycline, mometasone, mycophenolate mofetil, nabumetone, naproxen, oxaprozin, penicillamine, phenytoin, piroxicam, pomalidomide, pramoxine, prednisone, prednisolone, prednicarbate, primrose oil, resorcinol, rituximab, rofecoxib, salsalate, sulindac, sulfasalazine, tazarotene, tetracycline, tocilizumab, tofacitinib, tolmetin, tramadol, triamcinolone, trolamine salicylate, ustekinumab, valdecoxib, 3-(5-amino-2-methyl-4-oxo-4H-quinazolin-3-yl)-piperidine-2,6-dione, and (S)-3-(4-((4-(morpholinomethyl)benzyl)oxy)-1-oxoisoindolin-2-yl)piperidine-2,6-dione.

In some embodiments, the one or more selective active agents is selected from the group consisting of a Btk inhibitor, a cereblon targeting agent, a Tyk2 inhibitor, a Syk inhibitor, a JNK inhibitor, a MK2 inhibitor, a ERP5 inhibitor, a PD-1 inhibitor, a TIMP-3 inhibitor, a IKK-2 inhibitor, a LH2B inhibitor, a PKC-theta inhibitor, a IRAK4 inhibitor, a ROCK inhibitor, and a ROR-gamma-T inhibitor.

Administration of apremilast and a second active agent to a patient can occur simultaneously or sequentially by the same or different routes of administration. The suitability of a particular route of administration employed for a particular second active agent will depend on the second active agent itself (e.g., whether it can be administered orally or topically without decomposition prior to entering the blood stream) and the subject being treated. Particular routes of administration for the second active agents or ingredients are known to those of ordinary skill in the art. See, e.g., *The Merck Manual*, 448 (17th ed., 1999).

The amount of second active agent administered can be determined based on the specific agent used, the subject being treated, the severity and stage of disease and the amount(s) of apremilast and any optional additional second active agents concurrently administered to the patient. Those of ordinary skill in the art can determine the specific amounts according to conventional procedures known in the art. In the beginning, one can start from the amount of the second active agent that is conventionally used in the therapies and adjust the amount according to the factors described above. See, e.g., *Physician's Desk Reference* (59th Ed., 2005).

In certain embodiments, the second active agent is administered orally, topically, intravenously or subcutaneously and once to four times daily in an amount of from about 1 to about 1,000 mg, from about 5 to about 500 mg, from about 10 to about 350 mg or from about 50 to about 200 mg. The specific amount of the second active agent will depend on the specific agent used, the age of the subject being treated, the severity and stage of disease and the amount(s) of apremilast and any optional additional second active agents concurrently administered to the patient.

4.3 Apremilast

Without being limited by theory, apremilast is believed to be (+) enantiomer of 2-[1-(3-ethoxy-4-methoxyphenyl)-2-methanesulfonylethyl]-4-acetylaminoisoindolin-1,3-dione having the following structure:

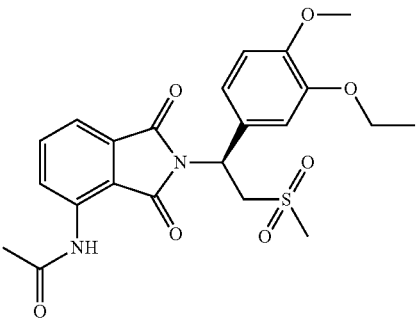 [SMILES: CCOc1cc([C@@H](CS(C)(=O)=O)N2C(=O)c3cccc(NC(C)=O)c3C2=O)ccc1OC]

Apremilast may be prepared according to methods disclosed in U.S. Pat. Nos. 6,962,940; 7,208,516; 7,427,638; or 7,893,101, the entirety of each which is incorporated herein by reference. In a specific method, apremilast may be prepared, for example, by the following process.

A stirred solution of 1-(3-ethoxy-4-methoxyphenyl)-2-methylsulfonylethylamine (1.0 g, 3.7 mmol) and 3-acetamidophthalic anhydride (751 mg, 3.66 mmol) in acetic acid (20 mL) was heated at reflux for 15 h. The solvent was removed in vacuo to yield an oil. Chromatography of the resulting oil yielded the product as a yellow solid (1.0 g, 59% yield): mp, 144° C.; $^1$H NMR (CDCl$_3$) δ: 1.47 (t, J=7.0 Hz, 3H, CH$_3$), 2.26 (s, 3H, CH$_3$), 2.88 (s, 3H, CH$_3$), 3.75 (dd, J=4.4, 14.3 Hz, 1H, CH), 3.85 (s, 3H, CH3), 4.11 (q, J=7 Hz, 2H, CH$_2$), 5.87 (dd, J=4.3, 10.5 Hz, 1H, NCH), 6.82-6.86 (m, 1H, Ar), 7.09-7.11 (m, 2H, Ar), 7.47 (d, J=7 Hz, 1H, Ar), 7.64 (t, J=8 Hz, 1H, Ar), 8.74 (d, J=8 Hz, 1H, Ar), 9.49 (br s, 1H, NH); $^{13}$C NMR (CDCl$_3$) δ: 14.61, 24.85, 41.54, 48.44, 54.34, 55.85, 64.43, 111.37, 112.34, 115.04, 118.11, 120.21, 124.85, 129.17, 130.96, 136.01, 137.52, 148.54, 149.65, 167.38, 169.09, 169.40; Anal Calc'd. for C$_{22}$H$_{24}$NO$_7$S: C, 57.38; H, 5.25; N, 6.08. Found: C, 57.31; H, 5.34; N, 5.83.

Preparation of 3-aminophthalic acid: 10% Pd/C (2.5 g), 3-nitrophthalic acid (75.0 g, 355 mmol) and ethanol (1.5 L) were charged to a 2.5 L Parr hydrogenator under a nitrogen atmosphere. Hydrogen was charged to the reaction vessel for up to 55 psi. The mixture was shaken for 13 hours, maintaining hydrogen pressure between 50 and 55 psi. Hydrogen was released and the mixture was purged with nitrogen 3 times. The suspension was filtered through a celite bed and rinsed with methanol. The filtrate was concentrated in vacuo. The resulting solid was reslurried in ether and isolated by vacuum filtration. The solid was dried in vacuo to a constant weight, affording 54 g (84% yield) of 3-aminopthalic acid as a yellow product. $^1$H-NMR (DMSO-d6) δ: 3.17 (s, 2H), 6.67 (d, 1H), 6.82 (d, 1H), 7.17 (t, 1H), 8-10 (br, s, 2H); $^{13}$C-NMR (DMSO-d6) δ: 112.00, 115.32, 118.20, 131.28, 135.86, 148.82, 169.15, 170.09.

Preparation of 3-aminophthalic anhydride: A 1 L 3-necked round bottom flask was equipped with a mechanical stirrer, thermometer, and condenser and charged with 3-aminophthalic acid (108 g, 596 mmol) and acetic anhydride (550 mL). The reaction mixture was heated to reflux for 3 hours and cooled to about 25° C. and further to 0-5° C. for another 1 hour. The crystalline solid was collected by vacuum filtration and washed with ether. The solid product was dried in vacuo at ambient temperature to a constant weight, giving 75 g (61% yield) of 3-acetamidopthalic anhydride as a white product. $^1$H-NMR (CDCl$_3$) δ: 2.21 (s, 3H), 7.76 (d, 1H), 7.94 (t, 1H), 8.42 (d, 1H), 9.84 (s, 1H).

Resolution of 2-(3-ethoxy-4-methoxyphenyl-1-(methylsulphonyl)-eth-2-ylamine: A 3 L 3-necked round bottom flask was equipped with a mechanical stirrer, thermometer, and condenser and charged with 2-(3-ethoxy-4-methoxyphenyl)-1-(methylsulphonyl)-eth-2-ylamine (137.0 g, 500 mmol), N-acetyl-L-leucine (52 g, 300 mmol), and methanol (1.0 L). The stirred slurry was heated to reflux for 1 hour. The stirred mixture was allowed to cool to ambient temperature and stirring was continued for another 3 hours at ambient temperature. The slurry was filtered and washed with methanol (250 L). The solid was air-dried and then dried in vacuo at ambient temperature to a constant weight, giving 109.5 g (98% yield) of the crude product (85.8% ee). The crude solid (55.0 g) and methanol (440 mL) were brought to reflux for 1 hour, cooled to room temperature and stirred for an additional 3 hours at ambient temperature. The slurry was filtered and the filter cake was washed with methanol (200 mL). The solid was air-dried and then dried in vacuo at 30° C. to a constant weight, yielding 49.6 g (90% recovery) of (S)-2-(3-ethoxy-4-methoxyphenyl)-1-(methylsulphonyl)-eth-2-ylamine-N-acetyl-L-leucine salt (98.4% ee). Chiral HPLC (1/99 EtOH/20 mM KH$_2$PO$_4$@pH 7.0, Ultron Chiral ES-OVS from Agilent Technologies, 150 mm×4.6 mm, 0.5 mL/min., @240 nm): 18.4 min (S-isomer, 99.2%), 25.5 min (R-isomer, 0.8%).

Final preparation of apremilast: A 500 mL 3-necked round bottom flask was equipped with a mechanical stirrer, thermometer, and condenser. The reaction vessel was charged with (S)-2-(3-ethoxy-4-methoxyphenyl)-1-(methylsulphonyl)-eth-2-yl amine N-acetyl-L-leucine salt (25 g, 56 mmol, 98% ee), 3-acetamidophthalic anhydride (12.1 g, 58.8 mmol), and glacial acetic acid (250 mL). The mixture was refluxed over night and then cooled to <50° C. The solvent was removed in vacuo, and the residue was dissolved in ethyl acetate. The resulting solution was washed with water (250 mL×2), saturated aqueous NaHCO$_3$ (250 mL×2), brine (250 mL×2), and dried over sodium sulphate. The solvent was evaporated in vacuo, and the residue recrystallized from a binary solvent containing ethanol (150 mL) and acetone (75 mL). The solid was isolated by vacuum filtration and washed with ethanol (100 mL×2). The product was dried in vacuo at 60° C. to a constant weight, affording 19.4 g (75% yield) of apremilast with 98% ee. Chiral HPLC (15/85 EtOH/20 mM KH$_2$PO$_4$@pH 5, Ultron Chiral ES-OVS from Agilent Technology, 150 mm×4.6 mm, 0.4 mL/min, @240 nm): 25.4 min (S-isomer, 98.7%), 29.5 min (R-isomer, 1.2%). $^1$H-NMR (CDCl$_3$) δ: 1.47 (t, 3H), 2.26 (s, 3H), 2.87 (s, 3H), 3.68-3.75 (dd, 1H), 3.85 (s, 3H), 4.07-4.15 (q, 2H), 4.51-4.61 (dd, 1H), 5.84-5.90 (dd, 1H), 6.82-8.77 (m, 6H), 9.46 (s, 1H); $^{13}$C-NMR (DMSO-d6) δ: 14.66, 24.92, 41.61, 48.53, 54.46, 55.91, 64.51, 111.44, 112.40, 115.10, 118.20, 120.28, 124.94, 129.22, 131.02, 136.09, 137.60, 148.62, 149.74, 167.46, 169.14, 169.48.

4.4 Pharmaceutical Compositions and Dosage Forms

Pharmaceutical compositions can be used in the preparation of individual, single unit dosage forms. Pharmaceutical compositions and dosage forms can comprise apremilast or a pharmaceutically acceptable salt or solvate thereof and a second active agent. Examples of the optional second active agents are disclosed herein (see, e.g., section 5.2.1). Pharmaceutical compositions and dosage forms can further comprise one or more carriers, excipients or diluents.

The pharmaceutical compositions provided herein are suitable for oral administration can be presented as discrete dosage forms, such as, but not limited to, tablets (e.g., chewable tablets), caplets, capsules and liquids (e.g., flavored syrups). Such dosage forms contain predetermined amounts of active ingredients and can be prepared by methods of pharmacy well known to those skilled in the art. See generally, *Remington's Pharmaceutical Sciences,* 20th ed., Mack Publishing, Easton Pa. (2,000).

Typical oral dosage forms are prepared by combining the active ingredients in an intimate admixture with at least one excipient according to conventional pharmaceutical compounding techniques. Excipients can take a wide variety of forms depending on the form of preparation desired for administration. Non-limiting examples of excipients suitable for use in oral liquid or aerosol dosage forms include water, glycols, oils, alcohols, flavoring agents, preservatives and coloring agents. Non-limiting examples of excipients suitable for use in solid oral dosage forms (e.g., powders, tablets, capsules and caplets) include starches, sugars, micro-crystalline cellulose, diluents, granulating agents, lubricants, binders and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers or both and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Non-limiting examples of excipients that can be used in oral dosage forms include binders, fillers, disintegrants and lubricants. Non-limiting examples of binders suitable for use in pharmaceutical compositions and dosage forms include corn starch, potato starch or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose and mixtures thereof.

Non-limiting examples of suitable forms of microcrystalline cellulose include, but are not limited to, the materials sold as AVICEL® (microcrystalline cellulose) PH-101, AVICEL® (microcrystalline cellulose) PH-103, AVICEL RC-581® (crystalline cellulose and carboxymethylcellulose sodium), AVICEL® (microcrystalline cellulose) PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581® (crystalline cellulose and carboxymethylcellulose sodium). Suitable anhydrous or low moisture excipients or additives include AVICEL-PH-103™® (microcrystalline cellulose) PH-103 and Starch 1500® LM (pregelatinized starch).

Non-limiting examples of fillers suitable for use in the pharmaceutical compositions and dosage forms disclosed herein include talc, calcium carbonate (e.g., granules or powder), microcrystalline cellulose, powdered cellulose, dextrates, kaolin, mannitol, silicic acid, sorbitol, starch, pre-gelatinized starch and mixtures thereof. The binder or filler in pharmaceutical compositions is typically present in from about 50 to about 99 weight percent of the pharmaceutical composition or dosage form.

Disintegrants are used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms. The amount of disintegrant used varies based upon the type of formulation and is readily discernible to those of ordinary skill in the art. Typical pharmaceutical compositions comprise from about 0.5 to about 15 weight percent of disintegrant, preferably from about 1 to about 5 weight percent of disintegrant.

Non-limiting examples of disintegrants that can be used in pharmaceutical compositions and dosage forms include agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums and mixtures thereof.

Non-limiting examples of lubricants that can be used in pharmaceutical compositions and dosage forms include calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil and soybean oil), zinc stearate, ethyl oleate, ethyl laureate, agar and mixtures thereof. Additional lubricants include, for example, a syloid silica gel (AEROSIL200® (silica), manufactured by W.R. Grace Co. of Baltimore, Md.), a coagulated aerosol of synthetic silica (marketed by Degussa Co. of Plano, Tex.), CAB-Co-Sift (fumed silica) (a pyrogenic silicon dioxide product sold by Cabot Co. of Boston, Mass.) and mixtures thereof. If used at all, lubricants are typically used in an amount of less than about 1 weight percent of the pharmaceutical compositions or dosage forms into which they are incorporated.

Non-limiting examples of dosage forms include tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions or a water-in-oil liquid emulsions), solutions and elixirs.

The composition, shape and type of dosage forms will typically vary depending on their use. For example, a dosage form used in the acute treatment of a disease may contain larger amounts of one or more of the active ingredients it comprises than a dosage form used in the chronic treatment of the same disease. These and other ways in which specific dosage forms will vary from one another will be readily apparent to those skilled in the art. See, e.g., *Remington's Pharmaceutical Sciences*, 20th ed., Mack Publishing, Easton Pa. (2,000).

Typical pharmaceutical compositions and dosage forms comprise one or more excipients. Suitable excipients are well known to those skilled in the art of pharmacy and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. The suitability of a particular excipient may also depend on the specific active ingredients in the dosage form. For example, the decomposition of some active ingredients can be accelerated by some excipients such as lactose or when exposed to water. Active ingredients that comprise primary or secondary amines are particularly susceptible to such accelerated decomposition.

In certain embodiments, provided herein are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice*, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment and use of formulations.

Anhydrous pharmaceutical compositions and dosage forms can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Non-limiting examples of suitable packaging include hermetically sealed foils, plastics, unit dose containers (e.g., vials), blister packs and strip packs.

Also provided herein are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers or salt buffers. Like the amounts and types of excipients, the amounts and specific types of active ingredients in a dosage form may differ depending on factors such as, but not limited to, the route by which it is to be administered to patients. However, typical oral dosage forms comprise apremilast in an amount of 10 mg, 20 mg or 30 mg. In a particular embodiments, the oral dosage forms are 10 mg, 20 mg or 30 mg tablets.

4.5 Delayed Release Dosage Forms

In certain embodiments, active ingredients can be administered by controlled release means or by delivery devices that are well known to those of ordinary skill in the art. Non-limiting examples of controlled release means or delivery devices include those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556 and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres or a combination thereof to provide the desired release profile in varying proportions. Suitable controlled-release formulations known to those of ordinary skill in the art, including those described herein, can be readily selected for use with the active ingredients. In certain embodiments, provided herein are single unit dosage forms suitable for oral administration such as, but not limited to, tablets, capsules, gelcaps and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency and increased patient compliance. In addition, controlled-release formulations can be used to affect the time of onset of action or other characteristics, such as blood levels of the drug and can thus affect the occurrence of side (e.g., adverse) effects.

Most controlled-release formulations are designed to initially release an amount of drug (active ingredient) that promptly produces the desired therapeutic effect and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water or other physiological conditions or compounds.

5. EXAMPLES

Some embodiments are illustrated by the following non-limiting examples. The examples should not be construed as a limitation in the scope thereof 5.1. Biological Activity of Apremilast in Patients with Psoriatic Arthritis in a Phase II Clinical Study A phase II, randomized, double-blind, placebo controlled, multicenter clinical study was performed in North America and Europe in patients with psoriatic arthritis (PsA). Two hundred subjects were enrolled (mean age of 51 years old; 53% male and 47% female). Mean duration of PsA was 7.8 years; mean tender joint count of 22, mean swollen joint count of 10 at baseline (Moll & Wright criteria). Baseline characteristics were well-balanced between treatment groups. Patients were randomized with Apremilast in an amount of 20 mg twice per day, 40 mg once per day, or placebo for 12 weeks. Stable doses of NSAIDs, corticosteroids (≤10 mg/day prednisone or equivalent), and methotrexate were allowed. A total of 126 subjects were then treated in an active-drug extension for 12 weeks (24 weeks total) including 40 placebo subjects who received the two dose regimens of apremilast in a 1:1 ratio.

Results:

One hundred sixty eight subjects completed the 12 week treatment phase. Primary endpoint, ACR20 at 12 weeks, was met by 20 mg BID and 40 mg QD doses of apremilast. Efficacy results are given in the table below. In evaluable subjects, response was maintained at 24 weeks (ACR20 40% and 39.1% for 20 mg BID and 40 mg QD, respectively). Placebo subjects switched to apremilast in the extension achieved similar responses at 24 weeks to subjects originally allocated to apremilast (ACR20 35% and 40% for placebo to 20 mg BID and placebo to 40 mg QD, respectively).

The 5 most common adverse events (AEs) were nausea, diarrhea, headache, nasopharyngitis, and fatigue. Discontinuations due to AEs were 9% and 6% of apremilast subjects (20 mg BID, 40 mg QD, respectively), versus 3% in placebo group. Discontinuations due to lack of efficacy were 7 and 0% of apremilast subjects (20 mg BID, 40 mg QD, respectively), vs 15% in the placebo group. Eight subjects reported a serious AE (SAE) during the 12 week study period (4 in 20 mg BID, 0 in 40 mg QD, 4 in placebo); 7 subjects reported an SAE in the extension. There was no obvious difference in infections between apremilast and placebo groups and there were no deaths.

Conclusion:

The study results showed that apremilast significantly improved signs and symptoms of PsA. The majority of adverse events were mild to moderate and did not lead to discontinuation. The results were very promising and consistent with efficacy and safety of apremilast in PsA patients.

5.2 Biological Activity of Apremilast in Patients with Psoriatic Arthritis in Phase III Clinical Studies The safety and efficacy of apremilast was evaluated in three multi-center, randomized, double-blind, placebo-controlled trials (Studies PALACE 1, PALACE 2, and PALACE 3) of similar design. A total of 1493 adult patients with active PsA (≥3 swollen joints and ≥3 tender joints) despite prior or current treatment with disease-modifying antirheumatic drug (DMARD) therapy were randomized. Patients enrolled in these studies had a diagnosis of PsA for at least 6 months. One qualifying psoriatic skin lesion of at least 2 cm in diameter was required in PALACE 3. Previous treatment with a biologic, including TNF-blockers was allowed.

Across the 3 studies, patients were randomly assigned to placebo (n=496), apremilast 20 mg (n=500), or apremilast 30 mg (n=497) given orally twice daily. Patients were allowed to receive stable doses of concomitant methotrexate (MTX) (≤25 mg/week), sulfasalazine (SSZ) (≤2 g/day), leflunomide (LEF) (≤20 mg/day), low dose oral corticosteroids (equivalent to ≤10 mg of prednisone a day), and/or nonsteroidal anti-inflammatory drugs (NSAIDs) during the trial. Treatment assignments were stratified based on small-molecule DMARD use at baseline. The patients who were therapeutic failures of >3 agents for PsA (small molecules or biologics), or >1 biologic TNF blocker were excluded.

The primary endpoint was the percentage of patients achieving American College of Rheumatology (ACR) 20 response at Week 16. Placebo-controlled efficacy data were collected and analyzed through Week 24. Patients with each subtype of PsA were enrolled across the 3 studies, including symmetric polyarthritis (62.0%), asymmetric oligoarthritis (26.9%), distal interphalangeal (DIP) joint arthritis (6.2%), arthritis mutilans (2.7%), and predominant spondylitis (2.1%). The median duration of PsA disease was 5 years.

Patients received concomitant therapy with at least one DMARD (65.2%), MTX (54.5%), SSZ (9.0%), LEF (7.4%), low dose oral corticosteroids (13.9%), and NSAIDs (70.7%). Prior treatment with small-molecule DMARDs only was reported in 76.4% of patients and prior treatment with biologic DMARDs was reported in 22.4% of patients.

Results:

The percent of patients achieving ACR 20, 50 and 70 responses in PALACE 1 are presented in Table 1 below. Apremilast with or without DMARDs, compared with placebo with or without DMARDs resulted in significant improvements in signs and symptoms of PsA as demonstrated by the proportion of patients with an ACR 20 response at Week 16. Improvement in ACR 50 and ACR 70 responses were also demonstrated at Week 16. Responses were sustained through Week 24. Similar results were obtained in Studies PALACE 2 and PALACE 3.

TABLE 1

Proportion of Patients with ACR Responses in PALACE 1

| N[a] | Placebo ± DMARDS N = 168 | Apremilast ± DMARDS N = 168 |
|---|---|---|
| ACR 20 | | |
| Week 16 | 19.0% | 38.1% |
| Week 24 | 13.1% | 35.1% |
| ACR 50 | | |
| Week 16 | 6.0% | 16.1% |
| Week 24 | 4.2% | 19.0% |
| ACR 70 | | |
| Week 16 | 1.2% | 4.2% |
| Week 24 | 0.6% | 10.1% |

[a]N is number of randomized and treated patients

An ACR 20 response rate of 43.5% was observed at Week 24 in patients treated with apremilast 30 mg BID for up to 24 weeks independent of their response at Week 16. Placebo patients who were non-responders at Week 16 were considered non-responders at Week 24. Similar improvements were observed in Studies PALACE 2 and PALACE 3.

ACR 20 responses were higher in patients treated with apremilast than in patients treated with placebo when used alone or in combination with small molecule DMARDs. At Week 16, the response rate of patients treated with apremilast concomitant with DMARD was 33.0% (35/106 patients), as compared to 23.6% in the placebo+DMARD group (26/110). At Week 16, the response rate of patients treated with apremilast alone was 46.8% (29/62 patients), as compared to 10.3% in the placebo group (6/58).

A greater proportion of patients who achieved an ACR 20 response was observed with the use of apremilast, irrespective of prior small molecule or prior biologic DMARD use. At Week 16, the response rate of patients treated with apremilast who had previously been treated with small molecule and/or biologic DMARD was 26.8% (11/41 patients), as compared to 4.9% in the placebo+DMARD group (2/41). In biologic-naive patients, the response rate at Week 16 in those treated with apremilast concomitant with DMARD was 41.1% (51/124 patients), as compared to 23.3% in the placebo+DMARD group (28/120). Similar results were observed in Studies PALACE 2 and PALACE 3.

Apremilast 30 mg BID resulted in significantly greater improvement compared to placebo for each ACR component, compared to placebo at Weeks 16 and 24 in Study PALACE 1 (Table 2). Similar results were observed in Studies PALACE 2 and PALACE 3.

TABLE 2

Percent Improvement in ACR Components in PALACE 1

| | Placebo ± DMARDS (N* = 168) | | Apremilast 30 mg BID ± DMARDS (N* = 168) | |
|---|---|---|---|---|
| | Baseline Value | % Change | Baseline Value | % Change |
| Number of tender joints[a] | | | | |
| Week 16 | 20.0 | 9.04 | 20.0 | 43.17 |
| Week 24 | 20.0 | 0.00 | 20.0 | 44.83 |
| Number of swollen joints[b] | | | | |
| Week 16 | 10.0 | 16.67 | 12.0 | 50.00 |
| Week 24 | 10.0 | 14.36 | 12.0 | 50.00 |
| Subject's assessment of pain[c] | | | | |
| Week 16 | 64.0 | 10.17 | 59.0 | 26.00 |
| Week 24 | 64.0 | 8.45 | 59.0 | 27.67 |
| Subject's global assessment of disease activity[c] | | | | |
| Week 16 | 62.0 | 8.96 | 57.0 | 20.29 |
| Week 24 | 62.0 | 4.00 | 57.0 | 23.92 |
| Physician's global assessment of disease activity[c] | | | | |
| Week 16 | 57.0 | 13.18 | 57.0 | 42.31 |
| Week 24 | 57.0 | 12.74 | 57.0 | 35.90 |
| HAQ-DI[d] score | | | | |
| Week 16 | 1.250 | 7.69 | 1.250 | 20.00 |
| Week 24 | 1.250 | 6.25 | 1.250 | 20.00 |
| CRP[e] | | | | |
| Week 16 | 0.494 | 1.20 | 0.493 | 12.40 |
| Week 24 | 0.494 | 4.05 | 0.493 | 8.45 |

[a]Scale 0-78
[b]Scale 0-76
[c]VAS = Visual Analog Scale; 0 = best, 100 = worst
[d]HAQ-DI = Health Assessment Questionnaire-Disability Index; 0 = best, 3 = worst; measures the subject's ability to perform the following: dress/groom, arise, eat, walk, reach, grip, maintain hygiene, and maintain daily activity.
[e]CRP = C-Reactive Protein; Reference range 0-10 mg/dL
N* = reflects randomized patients; actual number of patients evaluable for each endpoint may vary by time point.

A greater number of patients treated with apremilast 30 mg BID achieved remission, as measured by a DAS28 (CRP), less than 2.6 compared to placebo at Weeks 16 and 24. At Week 16, 22 (13.1%) patients receiving apremilast 30 mg BID (N=168) with or without DMARDs scored less than 2.6 as measured by a DAS28(CRP), as compared to 6 (3.6%) of the placebo patients. At Week 24, 32 (19.0%) patients receiving apremilast 30 mg BID (N=168) with or without DMARDs scored less than 2.6 as measured by a DAS28 (CRP), as compared to 7 (4.2%) of the placebo patients. Similar results were observed for Studies PALACE 2 and PALACE 3.

Treatment with apremilast also resulted in improvement of dactylitis and enthesitis in patients with pre-existing dactylitis or enthesitis.

Treatment with apremilast 30 BID resulted in improvement in skin manifestations. Patients with psoriatic involvement of at least three percent body surface area (BSA) were evaluated for Psoriatic Area and Severity Index (PASI)-75 responses. In Study PALACE 3, at Week 16, there was a significantly greater proportion of patients achieving a 75% improvement in the PASI (PASI-75) in the apremilast group compared to the placebo group (22.2% vs. 7.9%, respectively). At Week 24, the proportions of patients achieving a PASI-75 in the apremilast group was significantly greater compared to the placebo group (25.6% vs. 11.2%, respectively). PASI-75 responses were higher in patients treated with TRADE NAME than in patients treated with placebo with or without background DMARD treatment. Similar responses were observed in Studies PALACE 1 and PALACE 2.

Apremilast also demonstrated a greater improvement compared to placebo in the change in mean Health Assessment Questionnaire Disability Index (HAQ-DI) score from baseline to Week 16 (−0.244 vs. −0.086, respectively, p=0.0017) in Study PALACE 1. In addition, there was a greater proportion of HAQ-DI responders (≥0.3 change from baseline) at Week 16 for apremilast group compared to the placebo group. Responses were sustained at Week 24. Similar results were observed in Studies PALACE 2 and PALACE 3.

Patients treated with apremilast also showed greater improvement from baseline in the Short Form Health Survey (SF-36v2) physical functioning domain and physical component summary score compared to patients treated with placebo. No worsening was observed in the mean change from baseline in the Mental Component Summary score (MCS).

All of the references cited herein are incorporated by reference in their entirety. While the methods provided herein have been described with respect to the particular embodiments, it will be apparent to those skilled in the art that various changes and modifications can be made without departing from the spirit and scope as recited by the appended claims.

The embodiments described above are intended to be merely exemplary and those skilled in the art will recognize or will be able to ascertain using no more than routine experimentation, numerous equivalents of specific compounds, materials and procedures. All such equivalents are considered to be within the scope and are encompassed by the appended claims.

What is claimed is:

1. A method of treating psoriatic arthritis, which comprises orally administering to a patient having psoriatic arthritis escalating doses of stereomerically pure (+)-2-[1-(3-ethoxy-4-methoxyphenyl)-2-methylsulfonylethyl]-4-acetylaminoisoindoline-1,3-dione, or a pharmaceutically acceptable polymorph, salt or solvate thereof, wherein the method consists of the following dosing schedule:
  (i) 10 mg in the morning on the first day of administration;
  (ii) 10 mg in the morning and 10 mg after noon on the second day of administration;
  (iii) 10 mg in the morning and 20 mg after noon on the third day of administration;
  (iv) 20 mg in the morning and 20 mg after noon on the fourth day of administration;
  (v) 20 mg in the morning and 30 mg after noon on the fifth day of administration; and
  (vi) 30 mg in the morning and 30 mg after noon on the sixth and every subsequent day of administration.

2. The method of claim 1, wherein the stereomerically pure (+)-2-[1-(3-ethoxy-4-methoxyphenyl)-2-methylsulfonylethyl]-4-acetylaminoisoindoline-1,3-dione comprises greater than about 90% by weight of (+) isomer based on the total weight percent of the compound.

3. The method of claim 1, wherein the stereomerically pure (+)-2-[1-(3-ethoxy-4-methoxyphenyl)-2-methylsulfonylethyl]-4-acetylaminoisoindoline-1,3-dione comprises greater than about 95% by weight of (+) isomer based on the total weight percent of the compound.

4. The method of claim 1, wherein the stereomerically pure (+)-2-[1-(3-ethoxy-4-methoxyphenyl)-2-methylsulfonylethyl]-4-acetylaminoisoindoline-1,3-dione comprises greater than about 96% by weight of (+) isomer based on the total weight percent of the compound.

5. The method of claim 1, wherein the stereomerically pure (+)-2-[1-(3-ethoxy-4-methoxyphenyl)-2-methylsulfonylethyl]-4-acetylaminoisoindoline-1,3-dione comprises greater than about 97% by weight of (+) isomer based on the total weight percent of the compound.

6. The method of claim 1, wherein the stereomerically pure (+)-2-[1-(3-ethoxy-4-methoxyphenyl)-2-methylsulfonylethyl]-4-acetylaminoisoindoline-1,3-dione comprises greater than about 98% by weight of (+) isomer based on the total weight percent of the compound.

7. The method of claim 1, wherein the stereomerically pure (+)-2-[1-(3-ethoxy-4-methoxyphenyl)-2-methylsulfonylethyl]-4-acetylaminoisoindoline-1,3-dione comprises greater than about 99% by weight of (+) isomer based on the total weight percent of the compound.

8. The method of claim 1, wherein the stereomerically pure (+)-2-[1-(3-ethoxy-4-methoxyphenyl)-2-methylsulfonylethyl]-4-acetylaminoisoindoline-1,3-dione is administered in tablet form.

9. The method of claim 8, wherein the tablet comprises a 10 mg, 20 mg or 30 mg dose of stereomerically pure (+)-2-[1-(3-ethoxy-4-methoxyphenyl)-2-methylsulfonylethyl]-4-acetylaminoisoindoline-1,3-dione.

10. The method of claim 9, wherein the tablet comprises a 10 mg dose of stereomerically pure (+)-2-[1-(3-ethoxy-4-methoxyphenyl)-2-methylsulfonylethyl]-4-acetylaminoisoindoline-1,3-dione.

11. The method of claim 9, wherein the tablet comprises a 20 mg dose of stereomerically pure (+)-2-[1-(3-ethoxy-4-methoxyphenyl)-2-methylsulfonylethyl]-4-acetylaminoisoindoline-1,3-dione.

12. The method of claim 9, wherein the tablet comprises a 30 mg dose of stereomerically pure (+)-2-[1-(3-ethoxy-4-methoxyphenyl)-2-methylsulfonylethyl]-4-acetylaminoisoindoline-1,3-dione.

13. The method of claim 1, further comprising administering to the patient a therapeutically effective amount of one or more second active agents.

14. The method of claim 13, wherein the one or more second active agents are selected from the group consisting of a nonsteroidal anti-inflammatory drug, an immnunosuppressant, a topical steroid, a glucocorticoid, a calcineurin inhibitor, a Cox-2 inhibitor, a TNF-alpha inhibitor, an antirheumatic, an antipsoriatic, an interleukin inhibitor, a narcotic analgesic combination, a salicylate, a glucocorticoid and a topical rubefacient.

15. The method of claim 13, wherein the second active agent is a nonsteroidal anti-inflammatory agent.

16. The method of claim 13, wherein second active agent is a disease-modifying antirheumatic agent.

17. The method of claim 13, wherein the one or more second active agents are selected from the group consisting of abatacept, acetaminophen, acetaminophen/hydrocodone, acetaminophen/tramadol, acitretin, adalimumab, alclometasone, alefacept, alemtuzumab, aloe vera, aluminum hydroxide/aspirin/calcium carbonate/magnesium hydroxide, amcinonide, ammonium lactate/urea, ammonium lactate/ halobetasol, anakinra, anthralin, aspirin, auranofin, aurothioglucose, atorvastatin, azathioprine, benzocaine/pyrilamine/zinc oxide, betamethasone, betamethasone/calcipotriene, calcipotriene, celecoxib, certolizumab, chondroitin, clobetasol, clocortolone, coal tar, coal tar/salicylic acid, corticotropin, cortisone, cyclophosphamide, cyclosporine, daclizumab, desonide, desoximetasone, dexamethasone, diclofenac, diclofenac/misoprostol, diflorasone, diflunisal, doxycycline, esomeprazole, esomeprazole/naproxen, etanercept, etodolac, famotidine, famotidine/ibuprofen, fenoprofen, fluocinonide, flurandrenolide, flurbiprofen, fostamatinib, glucosamine, gold sodium thiomalate, golimumab, halcinonide, halobetasol, hydrocortisone, hydrocortisone/pramoxine, hydroxyurea, hydroxychloroquine, ibuprofen, indomethacin, infliximab, interferon, interferon gamma-1b, ibrutinib, ketoprofen, lansoprazole, lansoprazole/naproxen, leflunomide, lenalidomide, levamisole, meclofenamate, meloxicam, methotrexate, methoxsalen, methylprednisone, methylprednisolone, methyl salicylate, minocycline, mometasone, mycophenolate mofetil, nabumetone, naproxen, oxaprozin, penicillamine, phenytoin, piroxicam, pomalidomide, pramoxine, prednisone, prednisolone, prednicarbate, primrose oil, resorcinol, rituximab, rofecoxib, salsalate, sulindac, sulfasalazine, tazarotene, tetracycline, tocilizumab, tofacitinib, tolmetin, tramadol, triamcinolone, trolamine salicylate, ustekinumab, valdecoxib, 3-(5-amino-2-methyl-4-oxo-4H-quinazolin-3-yl)-piperidine-2,6-dione, and (S)-3-(4-((4-(morpholinomethyl)benzyl)oxy)-1-oxoisoindolin-2-yl)piperidine-2,6-dione.

18. The method of claim 13, wherein the second active agent is methotrexate.

19. The method of claim 13, wherein the second active agent is sulfasalazine.

20. The method of claim 13, wherein the second active agent is leflunomide.

21. The method of claim 13, wherein the second active agent is etanercept.

22. The method of claim 13, wherein the second active agent is an oral corticosteroid.

23. The method of claim 22, wherein the second active agent is prednisone.

24. The method of claim 1, wherein the patient has received prior treatment for psoriatic arthritis.

25. The method of claim 24, wherein the prior treatment is with a disease-modifying antirheumatic drug.

26. The method of claim 24, wherein the psoriatic arthritis is refractory to the prior treatment.

27. The method of claim 1, wherein psoriatic arthritis is symmetric polyarthritis, asymmetric oligoarthritis, distal interphalangeal joint arthritis, arthritis mutilans, or predominant spondylitis.

28. The method of claim 1, which comprises administering stereomerically pure (+)-2-[1-(3-ethoxy-4-methoxyphenyl)-2-methylsulfonylethyl]-4-acetylaminoisoindoline-1,3-dione, substantially free of any salt or solvate forms of (+)-2-[1-(3-ethoxy-4-methoxyphenyl)-2-methylsulfonylethyl]-4-acetylaminoisoindoline-1,3-dione.

29. The method of claim 1, which comprises administering a pharmaceutically acceptable salt of stereomerically pure (+)-2-[1-(3-ethoxy-4-methoxyphenyl)-2-methylsulfonylethyl]-4-acetylaminoisoindoline-1,3-dione.

30. The method of claim 1, which comprises administering a pharmaceutically acceptable solvate of stereomerically pure (+)-2-[1-(3-ethoxy-4-methoxyphenyl)-2-methylsulfonylethyl]-4-acetylaminoisoindoline-1,3-dione.

\* \* \* \* \*